United States Patent [19]

Kawajiri et al.

[11] Patent Number: 5,442,108
[45] Date of Patent: Aug. 15, 1995

[54] PROCESS FOR REMOVAL OF SOLID ORGANIC MATTERS

[75] Inventors: Tatsuya Kawajiri; Hideyuki Hironaka; Kazuyuki Uekawa; Michio Tanimoto; Hiromi Yunoki; Tsuyoshi Kudoh, all of Himeji, Japan

[73] Assignee: Nippon Shokubai Co., Ltd., Osaka, Japan

[21] Appl. No.: 208,667

[22] Filed: Mar. 11, 1994

[30] Foreign Application Priority Data

Mar. 12, 1993 [JP] Japan .................. 5-051874
Mar. 12, 1993 [JP] Japan .................. 5-051875

[51] Int. Cl.$^6$ .................................. C07C 51/16
[52] U.S. Cl. .................................. 562/532; 562/535
[58] Field of Search .......................... 562/532

[56] References Cited

U.S. PATENT DOCUMENTS

| | | | |
|---|---|---|---|
| 3,755,202 | 8/1973 | Katsobashvili et al. | 252/417 |
| 4,751,210 | 6/1988 | de Agudelo et al. | 502/51 |
| 4,942,258 | 7/1990 | Smith | 562/599 |

FOREIGN PATENT DOCUMENTS

| | | |
|---|---|---|
| 44-26287 | 3/1969 | Japan . |
| 50-8360 | 3/1972 | Japan . |
| 47-33082 | 4/1972 | Japan . |
| 48-16493 | 3/1973 | Japan . |
| 50-97592 | 11/1975 | Japan . |
| 51-70719 | 4/1976 | Japan . |
| 51-70718 | 11/1976 | Japan . |
| 53-113790 | 3/1978 | Japan . |
| 53-43917 | 4/1978 | Japan . |
| 53-30688 | 11/1978 | Japan . |
| 54-2293 | 5/1979 | Japan . |
| 57-54172 | 6/1982 | Japan . |
| 58-156351 | 11/1983 | Japan . |
| 62-17578 | 2/1987 | Japan . |
| 63-42738 | 1/1988 | Japan . |
| 63-51353 | 1/1988 | Japan . |
| 63-93747 | 11/1988 | Japan . |
| 64-63543 | 11/1989 | Japan . |

*Primary Examiner*—Paul J. Killos
*Attorney, Agent, or Firm*—Sherman and Shalloway

[57] ABSTRACT

A process for removal of solid organic matters formed and deposited in the reaction system when an unsaturated aldehyde or an unsaturated aidehyde-containing gas is subjected to catalytic gaseous oxidation in the presence of an oxidizing catalyst to prepare an unsaturated carboxylic acid corresponding thereto, which process comprises contacting the solid organic matters with a mixed gas containing at least 3 volume % of molecular oxygen and at least 0.1 volume % of steam at a temperature of 260° to 450° C.

20 Claims, No Drawings

PROCESS FOR REMOVAL OF SOLID ORGANIC MATTERS

This invention relates to a process for safe and efficient removal of solid organic matters formed and deposited in instruments such as the piping and the reactor in the reaction system or on the oxidizing catalyst layer in the catalytic gaseous oxidation reaction of an unsaturated aidehyde or an unsaturated aidehyde-containing gas. Further, this invention relates to a process for efficient regeneration of an oxidizing catalyst whose catalytic activity was lowered by reduction caused by performance of oxidation reaction over a long term, without causing any damage due to its complete oxidation.

Many proposals have hitherto been made on a process for preparation of an unsaturated carboxylic acid from a corresponding unsaturated aidehyde or a corresponding unsaturated aidehyde-containing gas by catalytic gaseous oxidation reaction. For example, there can be mentioned Japanese Patent Publication Nos. 16493/1973, 30688/1978 and 17578/1987, Japanese Laid-Open Patent Publication Nos. 51353/1988 and 93747/1988, etc. for reaction conditions therefor, and Japanese Patent Publication Nos. 26287/1969, 8360/1972, 43917/1978 and 54172/1982, Japanese Laid-Open Patent Publication Nos. 8360/1972, 97592/1975, 70718/1976 and 70719/1976, etc. for oxidizing catalysts therefor.

However, it is the actual state of things that none of these proposals aims at preparation of unsaturated carboxylic acids in high yields, and therefore cannot solve problems at all encountered in performance of the catalytic gaseous oxidation reaction in an industrial scale, that is, blocking of the piping, pressure loss in the reactor, etc. caused by solid organic matters, solid carbides, etc. (in this invention, these are generically referred to as "solid organic matters") formed and deposited in the reaction system due to the unsaturated aidehyde or the unsaturated aidehyde-containing gas as the raw material gas, impurities in this raw material gas or by-products by the reaction.

More detailedly, these solid organic matters are formed in the piping for connection of one reactor with the other reactor, the portion for quenching of the reaction gas, or the portion for preheating of the oxidizing catalyst layer, or in some case on the oxidizing catalyst in the reaction system, and are deposited thereon, and cause blocking of each portion of the plant or abnormally increase pressure loss to hinder the running of the plant, or even have a danger to cause abnormal heat evolution or ignition at the time of stop or reoperation of the plant. It is the present state of things against these problems that the running of the plant is regularly stopped, removal of the solid organic matters and cleaning are made by physical labor, and washing of the portions of formation thereof is made, but such process is very inefficient both in respect of energy and time.

Further, when solid organic matters are formed and deposited on the oxidizing catalyst, the catalytic activity lowers, and the yield of the desired unsaturated carboxylic acid lowers. As for processes for regeneration of oxidizing catalysts whose catalytic activity was lowered by various reasons, there are proposals, for example in Japanese Laid-Open Patent Publication Nos. 33082/1972, 2293/1979, 113790/1978, 156351/1983 and 2738/1988, etc.

However, processes proposed in Japanese Laid Open Patent Publication Nos. 33082/1972, 2293/1979 and 113790/1978, etc. are those which comprise once extracting the catalyst packed in the reactor and regenerating it through complicated operations, and cannot be said to be ones fully satisfactory in the aspects of regeneration efficiency, treatment operation and economy. Further, in Japanese Laid-Open Patent Publication Nos. 156351/1983 and 42738/1988, processes which comprise reoxidizing the catalyst in a state such that the catalyst is packed in the reactor to regenerate it are proposed, but in these processes, catalysts and reactions as subjects thereof are limited to extremely narrow ranges, and moreover when the lowering of the catalytic activity is due to adsorption of by-products, regeneration effect thereby is insufficient.

The object of this invention is to provide a process for safe and efficient removal of solid organic matters formed and deposited in the reaction system in preparation of an unsaturated carboxylic acid by catalytic gaseous oxidation of an unsaturated aidehyde corresponding thereto or a gas containing the unsaturated aidehyde.

Another object of this invention is to provide a process to regenerate an oxidizing catalyst whose catalytic activity was lowered by solid organic matters formed and deposited on the oxidizing agent, by removing the solid organic matters safely and efficiently.

Another object of this invention is to provide a process for efficient regeneration of an oxidizing catalyst whose catalytic activity was lowered by reduction caused by performance of catalytic gaseous oxidation reaction over a long term, without causing any damage due to its complete oxidation.

The present inventors have researched for safe and efficient removal of the solid organic matters, and have found that in the presence of oxygen at a high temperature, the solid organic matters are removed from the system, but at that time cause large heat evolution to give large damage to the reactor and the catalyst packed therein. The present inventors have gone ahead with their researches, and as a result have found that the removal of the solid organic matters can be made safely and efficiently by making steam coexist in an oxygen-containing gas of a high temperature, and have completed this invention based on this finding.

Thus, according to this invention is provided a process for removal of solid organic matters, i.e. materials, formed and deposited in the reaction system when an unsaturated aidehyde or an unsaturated aidehyde-containing gas is subjected to catalytic gaseous oxidation in the presence of an oxidizing catalyst to prepare an unsaturated carboxylic acid corresponding thereto, which process comprises contacting the solid organic matters with a mixed gas containing at least 3 volume % of molecular oxygen and at least 0.1 volume % of steam at a temperature of 260° to 450° C.

According to this invention is further provided a process for regeneration of an oxidizing catalyst when an unsaturated aidehyde or an unsaturated aidehyde-containing gas is subjected to catalytic gaseous oxidation in the presence of the oxidizing catalyst to prepare an unsaturated carboxylic acid corresponding thereto, which process comprises contacting the oxidizing agent whose catalytic activity was lowered by reduction with a mixed gas containing at least 3 volume % of molecular oxygen and at least 0.1 volume % of steam at a temperature of 260° to 450° C.

As representative examples of the unsaturated aldehydes used as the raw material gas in this invention, there can be mentioned acrolein and methacrolein (hereafter referred to as (meth)acrolein). Further, as a representative example of the unsaturated aidehyde-containing gas, there can be mentioned a (meth)acrolein-containing gas. As this (meth)acrolein or (meth)acrolein-containing gas, there can be used a (meth)acrolein-mixed gas obtained by catalytic gaseous oxidation of propylene or at least one compound selected from isobutylene, t-butanol and methyl t-butyl ether, or (meth)acrolein separated from this mixed gas.

There is no particular limitation about the oxidizing catalyst used in the catalytic gaseous oxidation of the above raw material gas, and there can be used those usually used in this kind of reaction, for example a composite oxide catalyst containing molybdenum, vanadium, etc. as indispensable components. Particularly, in the case of preparation of acrylic acid from acrolein or an acrolein-containing gas, oxidizing catalysts represented by the general formula

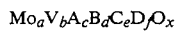

$Mo_aV_bA_cB_dC_eD_fO_x$ are particularly preferably used among those generally used as molybdenum-vanadium oxidizing catalysts for preparation of acrylic acid.

In the above general formula (I), Mo and V are molybdenum and vanadium, respectively, A is at least one element selected from tungsten and niobium, B is at least one element selected from iron, copper, nickel, antimony and chromium, C is at least one element selected from alkali metals and alkaline earth metals, D is one element selected from silicon, aluminum, titanium and zirconium, O is oxygen, and a, b, c, d, e, f and x denote atomic ratios of the respective elements, and in the case of $a=12$, b is $1-10$, c is $0-5$, d is $0-6$, e is $0-3$ and f is $0-6$, and x denotes an oxygen atom number necessary to satisfy the valences of the respective components.

First, in association with removal of solid organic matters formed and deposited in instruments such as the piping or the reactors in the reaction system, this invention is described detailedly. The "in instruments" referred to in this invention means portions with which the raw material gas or gas formed by the reaction directly contacts, among the reactor, and the equipments such as the quenching portion attached thereto, the preheating portion and the mixing vessel, and the piping used for performance of catalytic gaseous oxidation reaction of an unsaturated aidehyde or an unsaturated aidehyde-containing gas.

As molecular oxygen in the mixed gas for removal of the solid organic matters by contact therewith, there can be used pure oxygen, air, an oxygen-containing exhaust gas, or the like, but air is usually used. The ratio of molecular oxygen in the mixed gas is at least 3 volume %, preferably 3 to 20 volume %. When the ratio is smaller than 3 volume %, the solid organic matters cannot efficiently be removed. Further, there is no particular limitation about a source for generation of steam, and there can, for example, be used steam obtained by heating of pure water, steam accompanying an exhaust gas, or the like. The ratio of steam in the mixed gas is at least 0.1 volume %, preferably at least 0.5 volume %, and when the ratio is smaller than that, the solid organic matters cannot efficiently be removed. The ratio of steam in the mixed gas is particularly preferably 1 to 75 volume %. The mixed gas can be one consisting of molecular oxygen and steam, or one containing an inert gas such as nitrogen gas or carbon dioxide besides molecular oxygen and steam. The ratio of the inert gas in the mixed gas is 95 volume % or smaller, preferably 90 volume % or smaller. For example, a mixed gas consisting of 3 to 20 volume % of molecular oxygen, 1 to 75 volume % of steam and the residual inert gas is preferably used.

According to the process of this invention, the solid organic matters can be removed by contacting them with the above mixed gas at a temperature of 260 to 450° C. When the contact treatment temperature is lower than 260° C., sufficient removal cannot be made, and when the contact is carried out at a temperature above 450° C., there is a danger, fin some cases, that abnormal heat evolution is caused and the apparatus, etc. are damaged. The contact between the solid organic matters and the mixed gas is preferably carried out within the temperature range of 280° to 420° C.

As to treatment conditions for contact between the solid organic matters and the mixed gas, there is no particular limitation, and for example, the quantity of the mixed gas to be introduced (gas quantity) can appropriately be determined depending on the ability limit peculiar to the apparatus, and contact time can also appropriately be determined similarly, but usually, the treatment is stopped when the generation of oxidized carbon came not to be detected.

When solid organic matters formed in the reactor are removed by the process of this invention, it is sufficient to introduce the mixed gas from the inlet of this reactor. However, for example in a continuous process wherein acrolein is prepared by catalytic gaseous oxidation of propylene and successively this acrolein-mixed gas is subjected to catalytic gaseous oxidation to prepare acrylic acid, it is possible to remove, simultaneously, both solid organic matters formed in the acrolein oxidation reactor and solid organic matters formed in the piping between the acrolein oxidation reactor and the propylene oxidation reactor, by introducing the mixed gas from the inlet of the propylene oxidation reactor. Such an embodiment is included in this invention, too.

Next, description is made about a process to regenerate an oxidizing catalyst whose catalytic activity lowered, by removing solid organic matters formed and deposited on the oxidizing catalyst, and a process for regeneration of an oxidizing catalyst whose catalytic activity was lowered by reduction.

A molybdenum-vanadium oxidizing catalyst is generally used for preparation of acrylic acid by catalytic gaseous oxidation of acrolein or an acrolein-containing gas, but when solid organic matters are formed and deposited on this oxidizing catalyst, its catalytic activity is lowered. According to researches by the present inventors, it was revealed that adhesion of carbides is observed on the surface of the molybdenum-vanadium oxidizing catalyst whose catalytic activity lowered, and the metal oxide components on the surface of the catalyst are in a weak reduction state compared with the catalyst before use. These adhesion of carbides and weak reduction state become remarkable in proportion as the acrolein concentration in the reaction gas is hightened so that the productivity of acrylic acid can be increased, or in proportion as the oxygen concentration in the reaction gas is lowered and brought close to 0.5 of the theoretical oxygen ratio (oxygen/acrolein) necessary for formation of acrylic acid. As to the properties of the carbides adhering to the catalyst surface, they have a composition of 60 to 75 weight % of carbon, 20 to 30 weight % of oxygen and 1 to 3 weight % of hydrogen, and when heat treatment is carried out in the air, they decrease with heat evolution starting from 310° C. or so, and burn. However, simultaneously at the time of this combustion, the metal oxides on the catalyst surface get into a state of complete oxidation due to local high temperature caused by the combustion, and lose almost all of an ability to form acrylic acid by the catalytic partial oxidation of acrolein.

When a molybdenum-vanadium oxidizing catalyst whose activity lowered is regenerated by the process of this invention, it is sufficient to subject it to heat treatment under a stream of a mixed gas containing at least 3 volume % of molecular oxygen and at least 0.1 volume % of steam at a temperature within the range of 260° to 450° C., more preferably 310° to 420° C. It is possible, by this heat treatment, not only to remove the carbides without giving any damage due to rapid heat evolution, but to prevent complete oxidation of the metal oxides on the catalyst surface and recover the activity of the catalyst.

The ratio of molecular oxygen in the mixed gas is at least 3 volume %, preferably 3 to 19 volume %, more preferably 5 to 19 volume %. When the ratio of molecular oxygen is too small, the carbides adhering to the catalyst cannot sufficiently be removed. Further, the ratio of steam is at least 0.1 volume %, preferably 0.1 to 75 volume %, more preferably 0.3 to 75 volume %. When the ratio of steam is too small, rapid heat evolution takes place to completely oxidize the catalyst surface, and the catalytic activity can no longer be regenerated.

As the above molecular oxygen an steam, the same ones as above can be used. The mixed gas can either consist of molecular oxygen and steam, or contain an inert gas such as nitrogen gas or carbon dioxide gas as a component other than molecular oxygen and steam. The ratio of the inert gas in the above mixed gas can be 95 volume % or smaller, preferably 90 volume % or smaller. Namely, when a molybdenum-vanadium oxidizing catalyst whose catalytic activity lowered is regenerated, a mixed gas consisting of 3 to 19 volume % of molecular oxygen, 0.1 to 75 volume % of steam and 6 to 95 volume % of an inert gas is preferably used. In regeneration of a molybdenum-vanadium oxidizing catalyst whose catalytic activity lowered according to the process of this invention, when the heat treatment temperature is lower than 260° C., removal of the carbides becomes insufficient, and when the temperature is higher than 450° C., the catalyst surface is completely oxidized and regeneration of the catalytic activity becomes impossible. The above heat treatment is particularly preferably carried out at a temperature within the range of 310° to 420° C. For heat treatment within the above temperature range, usually, the mixed gas is heated to a predetermined temperature in advance and introduced into a reactor wherein an oxidizing catalyst layer was provided.

The quantity of the mixed gas to be introduced can be 100 to 5,000 hr$^{-1}$, preferably 200 to 3,000 hr$^{-1}$ as as an apparent space velocity (SU) (gas quantity/catalyst quantity ratio). When the space velocity (SV) is under 100 hr$^{-1}$ treatment efficiency is poor, and it is necessary to continue the treatment for a very long time for sufficient regeneration of the catalyst and such a space velocity is very disadvantageous for actual adoption. On the other hand, SV beyond 5,000 hr$^{-1}$ is not preferable because large energy becomes necessary for heating of the mixed gas used for the treatment, and moreover the catalyst packed in the reaction tube is sometimes blown out.

The process of this invention is preferably applied to a molybdenum-vanadium oxidizing catalyst whose catalytic activity lowered and, for example which is packed in a fixed bed multitubular reactor, but can also be applied to one in a floating state.

At the time of performance of this invention, for example in a continuous preparation process of acrylic acid consisting of a step for preparation of acrolein by catalytic gaseous oxidation reaction of propylene and a step for preparation of acrylic acid by catalytic gaseous oxidation reaction of acrolein obtained in this step, for regeneration of the molybdenum-vanadium catalyst packed in the fixed bed multitubular reactor of the latter step, it is possible either to introduce the mixed gas from the inlet of the reactor and heat treatment is carried out, or to introduce the mixed gas from the inlet of the fixed bed multitubular reactor for oxidation of propylene of the former step and heat treatment is carried out, and thus there is no particular limitation about the position of introduction of the mixed gas.

According to this invention, it is possible to remove safely and efficiently solid organic matters formed and deposited in the reaction system when an unsaturated aidehyde or an unsaturated aidehyde-containing gas is subjected to catalytic gaseous oxidation in an industrial scale to prepare a corresponding unsaturated carboxylic acid.

Further, in this occasion, it is possible to keep cooling and heating required for removal of the solid organic matters minimum and reduce wasteful consumption of energy.

According to this invention, the solid organic matters can be removed safely and efficiently, and therefore it is possible to solve problems such as blockage of the piping and pressure loss in the reactor caused by formation and deposition of the solid organic matters.

Further, according to this invention, the solid organic matters can be removed safely and efficiently, and therefore it is possible to efficiently regenerate a molybdenum-vanadium oxidizing catalyst whose catalytic activity was lowered by formation and deposition of the solid organic matters.

Further, according to this invention, it is possible to efficiently regenerate a molybdenum-vanadium oxidizing catalyst whose catalytic activity was lowered by formation and deposition of the solid organic matters, without withdrawing it from the reactor, i.e. with the catalyst being packed in the reactor.

Further, according to this invention, it is possible to efficiently regenerate a molybdenum-vanadium oxidizing catalyst whose catalytic activity was lowered by reduction caused by carrying out catalytic gaseous oxidation reaction over a long term, without causing any damage due to its complete oxidation.

This invention is further specifically described below according to examples.

Reference Example 1 (Preparation of Catalyst)

A propylene-oxidizing catalyst and an acrolein-oxidizing catalyst used for the reactions were prepared as follows according to the process disclosed in Example 1 of Japanese Laid-Open Patent Publication No. 63543/1989.

(a) 10.62 kg of ammonium molybdate and 3.24 kg of ammonium paratungstate were added to 15 liters of water heated, and the mixture was vigorously stirred to prepare a solution A. Separately, 7.00 kg of cobalt nitrate was dissolved in 2 liters of water, 2.43 kg of ferric nitrate was dissolved in 2 liters of water, and 2.92 kg of bismuth nitrate was dissolved in 3 liters of water acidified with 0.6 liter of concentrated nitric acid, and thereby three kinds of solutions were prepared. A solution obtained by mixing these three kinds of nitrate solutions was added dropwise to the solution A. Then, 2.44 kg of silica sol of a concentration of 20 weight % in terms of silicon dioxide and a solution obtained by dissolving 20.2 g of potassium hydroxide in 1.5 liters of water were added, the resultant suspension was heated to evaporate water, and the residue was molded into a column of diameter 5 mm and length 6 mm and burned at 450° C. for 6 hours under an air stream to prepare a propylene-oxidizing catalyst. The metal composition (atomic ratio) of this catalyst excluding the carrier was $Co_4Fe_1Bi_1W_2Mo_{10}Si_{1.35}K_{0.06}$.

(b) 1.25 kg of ammonium paratungstate, 1.03 kg of ammonium metavanadate, 4.06 kg of ammonium molybdate and 0.14 kg of ammonium dichromate were dissolved in 60 liters of water heated and stirred to prepare a solution B. Separately, an aqueous solution was prepared by dissolving 1.03 kg of copper nitrate in 0.72 liter of water, and this was mixed with the solution B. The resultant mixed solution was put in a stainless steel-made evaporator equipped with a steam heater, 12 liters of an δ-alumina-based spherical carrier of diameter 3 to 5 mm was added, and the mixture was evaporated to dryness to make the solutes adhere onto the carrier, and the resultant product was burned at 400° C. for 5 hours to prepare an acrolein-oxidizing catalyst. The metal composition (atomic ratio) of the catalyst excluding the carrier was $Mo_{12}V_{4.6}Cu_{2.2}Cr_{0.6}W_{2.4}$.

Reference Example 2 (Oxidation Reaction)

1.2 liters of the propylene-oxidizing catalyst of Reference example 1 was packed in a steel-made reaction tube of inner diameter 25 mm and length 3,000 mm. Separately, 1.0 liter of the acrolein-oxidizing catalyst of Reference example 1 was packed in a steel-made reaction tube of inner diameter 25 mm and length 3,000 mm. The two reaction tubes were connected by a steel-made pipe of inner diameter 20 mm, and the length of the pipe was 4,000 mm. Further, for preheating, magnetic rings of diameter 7.5 mm were packed over 500 mm at the reaction raw material gas inlet side of the acrolein-oxidizing reaction tube. A gas mixture of the composition consisting of 5 volume % of propylene, 10 volume % of oxygen, 25 volume % of steam and 60 volume % of nitrogen was introduced from the inlet of the reaction tube packed with the propylene-oxidizing catalyst, and reaction was carried out at a space velocity of 2,000 $hr^{-1}$ based on the propylene-oxidizing catalyst. At that time, the pipe connecting the two reaction tubes was kept at 170° C.

Example 1

When the oxidation of propylene was continued for 8,000 hours, deposition of carbides was observed in the pipe connecting the reaction tubes and the preheating layer portion of the acrolein-oxidizing reaction tube, and pressure loss in this portion increased by 50 mm Hg, compared with the time of the start of the reaction. The catalyst performance which was a propylene conversion of 98 mol % and an acrylic acid yield of 92 mol % at the initial stage of the reaction lowered to a propylene conversion of 92 mol % and an acrylic acid yield of 85 mol %.

When increase of the propylene conversion and the acrylic acid yield was aimed at by increasing the reaction temperature, abnormal high temperature was observed at the inlet side of the propylene-oxidizing catalyst layer, and there was a danger of occurrence of run away reaction, and thus the yield increase aimed at could not be attained. Therefore, the reaction was stopped and a mixed gas consisting of 10 volume % of oxygen, 50 volume % of steam and 40 volume % of nitrogen was flowed at 350° C. for 20 hours at a flow rate of 20 liters per minute (S.T.P.), and as a result the carbides deposited were completely removed and the pressure loss was brought back to the level at the initiation of the reaction. Further, during this treatment, there was no rapid increase of temperature at the carbides deposition portion. After the treatment, reaction was started again, and as a result was obtained performance of a propylene conversion of 98 mol % and an acrylic acid yield of 92.2 mol %.

Comparative Example 1

After the oxidation of propylene was continued for 8,000 hours, temperature was gradually increased from 250° C. while air was flowed into the reaction tube wherein the carbides deposited at a flow rate of 20 liter per minute, and as a result, suddenly at 280° C., the temperature of the carbides layer deposited rapidly increased and combustion of the carbides took place, and therefore, the treatment was discontinued.

Examples 2 to 5

The same treatments as in Example 1 were carried out except that the treatment conditions were changed in Example 1. The results are shown together with treatment conditions in Table 1.

TABLE 1

| Example | Mixed gas flow rate (liter/min) | Mixed gas composition (volume %) | | Treatment temperature (°C.) | Treatment time (hour) | Removal percentage* (%) | Maximum ΔT** (°C.) | Abnormal heat evolution, etc. |
|---|---|---|---|---|---|---|---|---|
| 2 | 10 | Oxygen | 3 | 420 | 20 | 98 | 10 | not observed |
|   |    | Steam | 10 | | | | | |
|   |    | Nitrogen | 87 | | | | | |
| 3 | 10 | Oxygen | 20 | 280 | 20 | 95 | 8 | not observed |
|   |    | Steam | 1 | | | | | |
|   |    | Nitrogen | 79 | | | | | |
| 4 | 20 | Oxygen | 10 | 300 | 40 | 99 | 7 | not observed |
|   |    | Steam | 20 | | | | | |
|   |    | Nitrogen | 70 | | | | | |

TABLE 1-continued

| Example | Mixed gas flow rate (liter/min) | Mixed gas composition (volume %) | | Treatment temperature (°C.) | Treatment time (hour) | Removal percentage* (%) | Maximum ΔT** (°C.) | Abnormal heat evolution, etc. |
| --- | --- | --- | --- | --- | --- | --- | --- | --- |
| 5 | 20 | Oxygen | 10 | 380 | 20 | 97 | 13 | not observed |
| | | Steam | 20 | | | | | |
| | | Nitrogen | 70 | | | | | |

*Removal percentage = (Weight of the carbides before the treatment − Weight of the carbides after the treatment)/(Weight of the carbides before the treatment) × 100
**Maximum ΔT = (maximum temperature of the carbides layer − treatment temperature)

Comparative Examples 2 to 5

The same treatments as in Example 1 were carried out except that the treatment conditions were changed in Example 1. The results are shown together with treatment conditions in Table 2.

TABLE 2

| Comparative example | Mixed gas flow rate (liter/min) | Mixed gas composition (volume %) | | Treatment temperature (°C.) | Treatment time (hour) | Removal percentage* (%) | Maximum ΔT** (°C.) | Abnormal heat evolution, etc |
| --- | --- | --- | --- | --- | --- | --- | --- | --- |
| 2 | 10 | Oxygen | 3 | 420 | 40 | 10 | 14 | not observed |
| | | Nitrogen | 97 | | | | | |
| 3 | 10 | Oxygen | 4 | 460 | 40 | 35 | 6 | not observed |
| | | Steam | 80 | | | | | |
| | | Nitrogen | 16 | | | | | |
| 4 | 10 | Oxygen | 20 | 250 | 40 | 30 | 3 | not observed |
| | | Steam | 1 | | | | | |
| | | Nitrogen | 79 | | | | | |
| 5 | 10 | Oxygen | 10 | 350 | 10 | — | ≧100 | Run away reaction occurred and continuation was impossible |
| | | Nitrogen | 90 | | | | | |

*Removal percentage = (Weight of the carbides before the treatment − Weight of the carbides after the treatment)/(Weight of the carbides before the treatment) × 100
**Maximum ΔT = (Maximum temperature of the carbides layer − treatment temperature)

Example 6

The same treatments as in Example 1 were carried out except that part of the mixed gas for the carbides treatment was used in circulation in Example 1. The mixed gas composition at the inlet of the reactor in this case was 10 volume % of oxygen, 50 volume % of steam, 0.5 to 1.0 volume % of carbon dioxide and the residual nitrogen. After the treatment for about 20 hours, the carbides were completely removed.

Reference example 3 (Preparation of Catalyst)

[Catalyst (1)]

250 g of ammonium paratungstate, 430 g of ammonium metavanadate, 1690 g of ammonium molybdate and 86 g of strontium nitrate were dissolved in 20 liters of water heated and stirred to prepare an aqueous solution A. Separately, 430 g of copper nitrate was dissolved in 5 liters of water to prepare an aqueous solution B. The solution A and the solution B were then mixed, the resultant mixed solution was impregnated into a carrier of diameter 4 to 6 mm composed of δ-alumina and carried thereon, and the mixture was then burned at 400° C. for 6 hours in an air atmosphere to obtain a catalyst (1). The metal composition (atomic ratio) of the catalytic components of this catalyst (1) were as follows.

$Mo_{12}V_{4.6}Sr_{0.5}W_{1.2}Cu_{2.2}$

[Catalysts (2) to (6)]

Catalysts (2) to (6) having the metal composition (atomic ratio) shown in Table 5 were prepared in the same manner as in the process for preparation of the catalyst (1).

Example 7

400 ml of the catalyst (1) was packed in a stainless steel-made U-tube of diameter 25 mm, the tube was immersed in a melted nitrate salt bath heated to 260° C., and an acrolein-containing reaction gas obtained by catalytic gaseous oxidation of propylene was introduced thereinto to carry out reaction continuously for 16,000 hours. The acrolein-containing reaction gas had a composition of 4.5 volume % of acrolein, 5 volume % of oxygen, 45 volume % of steam and 45.5 volume % of another gas containing nitrogen and accessorily formed organic compounds, and its space velocity (SV) was 2,000 hr$^{-1}$. At the initial stage of the reaction, at a reaction temperature of 260° C., the acrolein conversion was 99.5 mole % and the acrylic acid yield was 96.5 mole %, but after continuation of the reaction for 16,000 hours, at a reaction temperature of 295° C., the acrolein conversion was 97.5 mole % and the acrylic acid yield was 92.5 mole %, and thus lowering of the catalytic activity was observed. Therefore, the supply of the reaction gas was stopped, regeneration of the catalyst was carried out by holding the temperature at 320° C. for 20 hours while a mixed gas consisting of 60 volume % of steam and 40 volume % of air was introduced therein at a space velocity (SV) of 1,000 hr$^{-1}$, and then reaction was started again. As a result, at a reaction temperature of 263° C., the acrolein conversion and the acrylic acid yield were brought back to 99.7 mol % and 96.8 mole %, respectively.

The acrolein conversion and the acrylic acid yield were determined by the following equation. Acrolein conversion (mol %)=(mol number of acrolein reacted % mol number of acrolein supplied)×100 Acrylic acid yield (mol %)=(mol number of acrylic acid formed % mol number of acrolein supplied)×100

Comparative Example 6

The same regeneration treatment as in Example 7 was carried out except that air was used in place of the mixed gas consisting of 60 volume % of steam and 40 volume % of air in Example 7, and thereafter at a reaction temperature of 300° C. the acrolein conversion and the acrylic acid yield were measured. The results are shown in Table 3.

Comparative Example 7

The same regeneration treatment as in Example 7 was carried out except that a mixed gas consisting of 60 volume % of nitrogen and 40 volume % of air was used in place of the mixed gas consisting of 60 volume % of steam and 40 volume % of air in Example 7, and thereafter at a reaction temperature of 300° C. the acrolein conversion and the acrylic acid yield were measured. The results are shown in Table 3.

TABLE 3

| Comparative example | Elapsed time | Reaction temperature (°C.) | Acrolein conversion (mol %) | Acrylic acid yield (mol %) |
|---|---|---|---|---|
| 6 | Initial stage of reaction | 260 | 99.3 | 96.5 |
|   | After time lapse of 16,000 hours | 295 | 97.8 | 92.6 |
|   | After regeneration treatment | 300 | 96.0 | 89.7 |
| 7 | Initial stage of reaction | 260 | 99.5 | 96.8 |
|   | After time lapse of 16,000 hours | 295 | 97.6 | 92.3 |
|   | After regeneration treatment | 300 | 96.3 | 90.0 |

It is understood from the results of Table 3 that regeneration effect cannot be obtained when the treatment is carried out using air alone or the mixed gas consisting of air and nitrogen in place of the mixed gas of this invention.

Examples 8 to 13

The same regeneration treatment as in Example 7 was carried out except that the composition of the mixed gas, the space velocity (SV) of the mixed gas, the treatment temperature and the treatment time were changed in Example 7, and thereafter the acrolein conversion and the acrylic acid yield at the predetermined reaction temperature were measured. All the results are shown in Table 4.

TABLE 4

| Example | Mixed gas composition (volume %) | | | | Treatment temperature (°C.) | Treatment time (hr) | Space velocity (hr$^{-1}$) |
|---|---|---|---|---|---|---|---|
|   | Steam | Oxygen | Inert gas | | | | |
| 8 | 20 | 30 | nitrogen | 50 | 350 | 20 | 5000 |
| 9 | 1 | 15 | nitrogen | 76 | 310 | 40 | 1000 |
|   |   |   | carbon dioxide | 5 |   |   |   |
| 10 | 70 | 6 | nitrogen | 24 | 400 | 20 | 200 |
| 11 | 50 | 10 | nitrogen | 40 | 380 | 20 | 2000 |
| 12 | 0.3 | 10 | nitrogen | 89.7 | 320 | 20 | 2000 |
| 13 | 14 | 18 | nitrogen | 68 | 330 | 20 | 500 |

| Example | Reaction result | | | |
|---|---|---|---|---|
|   | Measurement time point | Reaction temperature (°C.) | Acrolein conversion (mol %) | Acrylic acid yield (mol %) |
| 8 | before treatment | 295 | 97.5 | 92.3 |
|   | after treatment | 265 | 99.6 | 96.1 |
| 9 | before treatment | 295 | 97.6 | 92.5 |
|   | after treatment | 265 | 98.9 | 95.8 |
| 10 | before treatment | 295 | 97.0 | 91.8 |
|   | after treatment | 265 | 99.2 | 95.5 |
| 11 | before treatment | 295 | 97.8 | 92.2 |
|   | after treatment | 265 | 99.5 | 96.0 |
| 12 | before treatment | 295 | 97.2 | 91.9 |
|   | after treatment | 265 | 99.0 | 95.8 |
| 13 | before treatment | 295 | 97.5 | 92.1 |
|   | after treatment | 265 | 99.2 | 95.7 |

Examples 14 to 18

The same reaction as in Example 7 was carried out using the catalysts (2), (3), (4), (5) or (6) place of the catalyst (1) in Example 7, and thereafter regeneration of the catalyst was carried out by holding the catalyst at 360° C. for 20 hours while a mixed gas consisting of 60 volume % of steam and 40 volume % of air was introduced at a space velocity (SV) of 2,000 hr$^{-1}$. Thereafter, the acrolein conversion and the acrylic acid yield at the predetermined reaction temperature were measured. All the results are shown in Table 5.

TABLE 5

| Example | Catalyst No. | Metal composition of catalyst components excluding carrier (atomic ratio) | Reaction result | | | |
|---|---|---|---|---|---|---|
|   |   |   | Elapsed time (hr) | Reaction temperature (°C.) | Acrolein conversion (mol %) | Acrylic acid yield (mol %) |
| 14 | 2 | Mo$_{12}$V$_5$Sb$_{1.5}$Ni$_4$W$_1$Cu$_1$ | Initial stage of reaction | 285 | 98.5 | 95.4 |
|   |   |   | 16,000 hours (before treatment) | 315 | 96.3 | 90.0 |

TABLE 5-continued

| Example | Catalyst No. | Metal composition of catalyst components excluding carrier (atomic ratio) | Elapsed time (hr) | Reaction temperature (°C.) | Acrolein conversion (mol %) | Acrylic acid yield (mol %) |
|---|---|---|---|---|---|---|
| | | | After treatment | 285 | 98.8 | 95.6 |
| 15 | 3 | $Mo_{12}V_3Nb_2Cu_1$ | Initial stage of reaction | 270 | 98.7 | 94.5 |
| | | | 16,000 hours (before treatment) | 300 | 95.3 | 89.3 |
| | | | After treatment | 275 | 98.5 | 94.3 |
| 16 | 4 | $Mo_{12}V_3W_3Fe_{2.5}Ti_4Ba_{0.1}$ | Initial stage of reaction | 270 | 98.5 | 94.8 |
| | | | 16,000 hours (before treatment) | 285 | 96.5 | 91.0 |
| | | | After treatment | 270 | 99.0 | 95.2 |
| 17 | 5 | $Mo_{12}V_6Nb_1Fe_3Zr_{0.5}$ | Initial stage of reaction | 270 | 99.0 | 93.5 |
| | | | 16,000 hours (before treatment) | 290 | 97.2 | 90.2 |
| | | | After treatment | 270 | 99.0 | 93.7 |
| 18 | 6 | $Mo_{12}V_4W_{2.5}Cu_1Fe_1Mg_{0.1}$ | Initial stage of reaction | 270 | 98.8 | 95.2 |
| | | | 16,000 hours (before treatment) | 300 | 96.0 | 90.1 |
| | | | After treatment | 270 | 98.6 | 95.4 |

Comparative Examples 8 to 12

The same regeneration treatment as in each of Examples 14 to 18 was carried out except that air was used in place of the mixed gas consisting of 60 volume % of steam and 40 volume % of air in each of Examples 14 to 18, and thereafter the acrolein conversion and the acrylic acid yield at the predetermined temperature were measured. All the results are shown in Table 6.

TABLE 6

| Comparative example | catalyst No. | Measurement time point | Reaction temperature (°C.) | Acrolein conversion (mol %) | Acrylic acid yield (mol %) |
|---|---|---|---|---|---|
| 8 | 2 | before treatment | 315 | 96.5 | 90.2 |
| | | after treatment | 320 | 94.0 | 87.5 |
| 9 | 3 | before treatment | 300 | 95.3 | 89.5 |
| | | after treatment | 300 | 90.5 | 82.7 |
| 10 | 4 | before treatment | 285 | 96.5 | 91.0 |
| | | after treatment | 295 | 95.4 | 90.1 |
| 11 | 5 | before treatment | 290 | 97.2 | 90.2 |
| | | after treatment | 290 | 95.2 | 88.6 |
| 12 | 6 | before treatment | 300 | 96.0 | 90.0 |
| | | after treatment | 300 | 95.4 | 88.9 |

It is understood from the results of Table 6 that regeneration effect cannot be obtained by using air in place of the mixed gas of this invention.

Comparative Example 13

The same regeneration treatment as in Example 7 was carried out except that a mixed gas consisting of 90 volume % of steam, 2 volume % of oxygen and 8 volume % of nitrogen was used in place of the mixed gas consisting of 60 volume % of steam and 40 volume % of air and was maintained at 420° C. for 20 hours in Example 7. The reaction was started again after the regeneration treatment, and as a result at a reaction temperature of 300° C. the acrolein conversion was 97.0 mole % and the acrylic acid yield was 91.6 mole %.

It is understood from the above result that regeneration effect cannot be obtained when the concentration of molecular oxygen in the mixed gas of this invention is under 3 volume %.

We claim:

1. A process for removal of solid organic materials formed and deposited in the reaction system when an unsaturated aldehyde or an unsaturated aidehyde-containing gas is subjected to catalytic gaseous oxidation in the presence of a molybdenum-vanadium oxidizing catalyst to prepare an unsaturated carboxylic acid corresponding thereto, which process comprises contacting the solid organic materials with a mixed gas containing at least 3 volume % of molecular oxygen and at least 0.1 volume % of steam at a temperature of 260° to 450° C.

2. The process according to claim 1 wherein the solid organic materials formed and deposited in instruments in the reaction system are removed.

3. The process according to claim 2 wherein the content of the molecular oxygen is 3 to 20 volume %.

4. The process according to claim 2 wherein the content of the steam is 1 to 75 volume %.

5. The process according to claim 2 wherein the catalytic treatment is carried out at a temperature within the range of 260° to 450° C.

6. The process according to claim 1 wherein the oxidizing catalyst is regenerated by removing the solid organic materials formed and deposited on the oxidizing catalyst in the reaction system.

7. The process according to claim 6 wherein the oxidizing catalyst consists essentially of a molybdenum-vanadium oxidizing catalyst.

8. The process according to claim 7 wherein the content of the molecular oxygen is 3 to 19 volume %.

9. The process according to claim 7 wherein the content of the steam is 0.1 to 75 volume %.

10. The process according to claim 7 wherein the catalytic treatment is carried out at a temperature within the range of 300° to 450° C.

11. The process according to claim 1 wherein the oxidizing catalyst is regenerated by contacting it with the mixed gas containing at least 3 volume % of molecular oxygen and at least 0.1 volume % of steam at a temperature of 260° to 450° C.

12. The process according to claim 11 wherein the oxidizing catalyst is a molybdenum-vanadium oxidizing catalyst which is a member selected from the group of catalyst consisting of
$Mo_{12}V_{4.6}Cu_{2.2}Cr_{0.6}W_{2.4}$,
$Mo_{12}V_{4.6}Sr_{0.5}W_{1.2}Cu_{2.2}$,
$Mo_{12}V_5Sb_{1.5}Ni_4W_1Cu_1$,
$Mo_{12}V_3Nb_2Cu_1$,
$Mo_{12}V_3W_3Fe_{2.5}Ti_4Ba_{0.1}$,
$Mo_{12}V_6Nb_1Fe_3Zr_{0.5}$, and
$Mo_{12}V_4W_{2.5}Cu_1Fe_1Mg_{0.1}$.

13. A process for removal of solid organic materials formed and deposited in the reaction system when an unsaturated aldehyde or an unsaturated aidehyde-containing gas is subjected to catalytic gaseous oxidation in the presence of an oxidizing catalyst consisting essentially of a molybdenum-vanadium catalyst to prepare an unsaturated carboxylic acid corresponding thereto, which process comprises contacting the solid organic materials with a mixed gas containing 3 to 20 volume % of molecular oxygen and 1 to 75 volume % of steam at a temperature of 260° to 450° C.

14. The process according to claim 13 wherein the oxidizing catalyst is regenerated by removing the solid organic materials formed and deposited on the oxidizing catalyst in the reaction system.

15. The process according to claim 13 wherein the catalytic treatment is carried out at a temperature within the range of 300° to 450° C.

16. The process according to claim 13 wherein the oxidizing catalyst is a molybdenum-vanadium oxidizing catalyst which is a member selected from the group of catalyst consisting of
$Mo_{12}V_{4.6}Cu_{2.2}Cr_{0.6}W_{2.4}$,
$Mo_{12}V_{4.6}Sr_{0.5}W_{1.2}Cu_{2.2}$,
$Mo_{12}V_5Sb_{1.5}Ni_4W_1Cu_1$,
$Mo_{12}V_3Nb_2Cu_1$,
$Mo_{12}V_3W_3Fe_{2.5}Ti_4Ba_{0.1}$,
$Mo_{12}V_6Nb_1Fe_3Zr_{0.5}$, and
$Mo_{12}V_4W_{2.5}Cu_1Fe_1Mg_{0.1}$.

17. A process for regenerating and removal of solid organic materials formed and deposited on an oxidizing catalyst consisting essentially of a molybdenum-vanadium catalyst when an unsaturated aldehyde or an unsaturated aidehyde-containing gas is subjected to catalytic gaseous oxidation in the presence of said oxidizing catalyst to prepare an unsaturated carboxylic acid corresponding thereto, which process comprises contacting the solid organic materials deposited on the catalyst with a mixed gas containing 3 to 20 volume % of molecular oxygen and 1 to 75 volume % of steam at a temperature of 260° to 450° C.

18. The process according to claim 17 wherein the catalyst treatment is carried out at a temperature within the range of 280° to 420° C.

19. The process according to claim 17 wherein the catalyst treatment is carried out at a temperature within the range of 310° to 420° C.

20. The process according to claim 17 wherein the oxidizing catalyst is a molybdenum-vanadium oxidizing catalyst which is a member selected from the group consisting of
$Mo_{12}V_{4.6}Cu_{2.2}Cr_{0.6}W_{2.4}$,
$Mo_{12}V_{4.6}Sr_{0.5}W_{1.2}Cu_{2.2}$,
$Mo_{12}V_5Sb_{1.5}Ni_4W_1Cu_1$,
$Mo_{12}V_3Nb_2Cu_1$,
$Mo_{12}V_3W_3Fe_{2.5}Ti_4Ba_{0.1}$,
$Mo_{12}V_6Nb_1Fe_3Zr_{0.5}$, and
$Mo_{12}V_4W_{2.5}Cu_1Fe_1Mg_{0.1}$.

* * * * *